United States Patent [19]

Elsheikh et al.

[11] Patent Number: 6,074,985
[45] Date of Patent: Jun. 13, 2000

[54] FLUORINATION CATALYSTS

[75] Inventors: Maher Y. Elsheikh; Bin Chen, both of Tredyffrin, Pa.

[73] Assignee: Elf Atochem North America, Inc., Philadelphia, Pa.

[21] Appl. No.: 09/369,307

[22] Filed: Aug. 3, 1999

[51] Int. Cl.[7] ............................. B01J 21/18; B01J 27/06; B01J 23/00; C07C 17/00; C07C 17/08

[52] U.S. Cl. ........................ 502/439; 502/182; 502/224; 502/227; 502/349; 502/350; 502/352; 502/353; 502/181; 570/165; 570/166; 570/167; 570/168; 570/169

[58] Field of Search .................................. 502/181, 182, 502/224, 227, 349, 350, 352, 353, 439; 570/165–169; 423/460

[56] References Cited

U.S. PATENT DOCUMENTS

| | | | |
|---|---|---|---|
| 2,749,374 | 6/1956 | Ruh et al. | 260/653 |
| 3,431,067 | 3/1969 | Kato et al. | 502/181 |
| 3,639,270 | 2/1972 | Koyanagi et al. | 502/80 |
| 3,673,113 | 6/1972 | Naito et al. | 502/181 |
| 4,469,804 | 9/1984 | Johnson | 502/32 |
| 4,474,895 | 10/1984 | Foulletier | 502/181 |
| 4,480,049 | 10/1984 | Johnson | 502/231 |
| 4,489,171 | 12/1984 | Johnson | 502/231 |
| 4,547,483 | 10/1985 | Muller et al. | 502/226 |
| 4,670,411 | 6/1987 | Johnson | 502/60 |
| 4,861,744 | 8/1989 | Sobolev | 502/227 |
| 5,116,592 | 5/1992 | Weinberg | 423/415.1 |
| 5,208,395 | 5/1993 | Elsheikh | 570/166 |
| 5,449,842 | 9/1995 | Elsheikh | 570/765 |
| 5,494,873 | 2/1996 | Tsuji et al. | 502/224 |
| 5,494,876 | 2/1996 | Tsuji et al. | 502/224 |
| 5,714,651 | 2/1998 | Elsheikh et al. | 570/165 |
| 5,811,603 | 9/1998 | Elsheikh | 570/166 |
| 5,849,658 | 12/1998 | Shibanuma et al. | 502/228 |
| 5,895,825 | 4/1999 | Elsheikh et al. | 570/167 |

*Primary Examiner*—Mark L. Bell
*Assistant Examiner*—Patricia L. Hailey
*Attorney, Agent, or Firm*—William D. Mitchell; Stanley A. Marcus

[57] ABSTRACT

A supported Lewis acid catalyst such as antimony V on a fluorine-treated moisture-free activated carbon support is provided, as are fluorination processes using such a catalyst.

2 Claims, No Drawings

FLUORINATION CATALYSTS

BACKGROUND OF THE INVENTION

This invention relates to novel catalysts useful in processes for the fluorination of hydrocarbons (halogenated or unsaturated), especially to supported Lewis acid catalysts such as antimony on fluorinated carbon which are useful at higher temperatures in such fluorination processes.

The art (for example, U.S. Pat. Nos. 5,449,842; 5,208,395; and 2,749,374) has disclosed the use of Lewis acid catalysts such as antimony (V) to catalyze fluorination processes involving the electrophilic addition of HF to unsaturated hydrocarbons or the replacement of a halogenated hydrocarbon's (non-fluorine) halogen atoms with fluorine atoms. However, in processes where the reaction temperature is greater than 150° C., antimony V is reduced to antimony III resulting in catalyst deactivation. Attempts to address this problem (as in the aforementioned U.S. Pat. No. 2,749,374) have involved the continuous feeding of low levels of chlorine to maintain antimony catalyst in the +5 oxidation state; this, however, causes the formation of undesirable chlorinated coproducts, which require separation and hence additional processing complications.

What is desired is a catalyst for use in fluorination processes which can withstand higher temperatures without the need for introducing additional cofeeds such as chlorine.

BRIEF SUMMARY OF THE INVENTION

A supported metal catalyst useful in fluorination processes is provided, the metal being selected from one or more of antimony, titanium, tin, niobium and tantalum (preferably antimony), the support being a fluorine treated moisture free activated carbon and the catalyst being activated with hydrogen fluoride prior to use, as are catalyzed fluorination processes using such supported metal catalysts.

DETAILED DESCRIPTION

It has now been discovered that the incorporation of a Lewis acid catalyst on a fluorine-treated, moisture-free activated carbon support results in a catalyst which enables fluorination to occur at higher temperatures (for example, 185° C.) without catalyst deactivation and without the need of introducing addtional reactants such as chlorine into the fluorination process.

While the preferred catalyst metal is antimony in the +5 oxidation state, the metal may also be titanium IV, tin IV, niobium V or tantalum V. Mixtures of one or more of the metals may also be employed. The metal concentration typically varies between 0.0001 and 0.1 moles per gram of catalyst, preferably 0.001–0.1 moles/gram.

The activated carbon support is heated to dryness (typically at about 180° C. in a stream of an inert gas such as nitrogen) and fluorine-treated. By "fluorine-treated" is meant that the dry activated carbon is contacted with a fluorinating agent such as hydrogen fluoride, $SF_4$, $SeF_4$, fluorine diluted with an inert gas such as nitrogen, or an interhalogen fluorine compound such as ClF, IF or $BrF_3$. The fluorinating agent can be added in the gas or liquid phase, batchwise or continuously. The temperature of addition is not critical and can, for example, be varied between room temperature (about 20° C.) and 200° C. An inert gas can be used with the fluorinating agent, but is not critical. The concentration of the fluorination agent used is typically between 0.01 and 10 grams per gram of catalyst.

The catalyst is subjected to normal activation procedures before use in a fluorination process, such as by feeding HF over the catalyst at about 50° C. for 24 hours.

The catalysts of this invention are useful in standard fluorination processes, such as continuous gas phase fluorinations, with a typical contact time of 0.1 to 60 seconds, and liquid phase batch fluorinations, with a typical contact time of 1 to 5 hours, except that the use of higher temperatures is now possible, as illustrated below in the following non-limiting examples.

EXAMPLE 1

Preparation of Antimony Catalyst on Fluorinated, Dry, Activated Carbon Support:

Activated carbon (Calgon CPG, 25 grams) was loaded into a reactor and heated at 180° C. in a stream of nitrogen for 24 hours. The reactor temperature was then lowered to 120° C. and HF liquid was fed at a rate of 0.11 grams/minute, together with nitrogen gas (100 ccm), for 24 hours, after which the reactor temperature was lowered to 50° C. Nitrogen was then fed at 40 ccm, together with 0.53 ccm of antimony (V) chloride for 10 minutes (12.6 grams). The catalyst was then activated at 50° C. with HF to prepare it for use in a fluorination process. EXAMPLE 2. Fluorination of 142$b$ (1-chloro-1,1-difluoroethane) to 143$a$ (1,1,1-trifluoroethane) at low and high temperatures using the activated catalyst of

EXAMPLE 1

To the activated catalyst was fed a gaseous mixture of HF (285 ccm) and 142$b$ (36 ccm) at 110° C. for a contact time of 3.5 seconds. Conversion was steady (90%) and selectivity for 143$a$ was 100%. When the temperature was increased to 185° C. (contact time of 7.5 seconds), conversion was 98% and selectivity for 143$a$ continued to be 100%. When the temperature was thereafter lowered back to 110° C. with a contact time of 3.5 seconds, the conversion again dropped to 90%, indicating that there was no loss of antimony V from the catalyst surface or reduction of antimony V to antimony III as a result of the use of higher temperatures. Also, upon opening the reactor and examining the catalyst, no evidence was found of deposited $SbF_3$.

What is claimed is:

1. A process for preparing activated carbon for use as a support for metal fluorination catalysts wherein the metal is selected from one or more of the group consisting of antimony V, titanium IV, tin IV, niobium V and tantalum V, said process consisting of subjecting the activated carbon to drying and treatment with a fluorinating agent.

2. A process as in claim 1 wherein the fluorinating agent is hydrogen fluoride.

* * * * *